United States Patent [19]
Eckert

[11] 4,372,893
[45] Feb. 8, 1983

[54] METHOD FOR REDUCTION OF REDUCIBLE GROUPS

[76] Inventor: Heiner Eckert, Lerchenauerstr. 9, D-8000 München 40, Fed. Rep. of Germany

[21] Appl. No.: 194,333

[22] Filed: Oct. 6, 1980

[30] Foreign Application Priority Data

Apr. 1, 1980 [DE] Fed. Rep. of Germany ....... 3012674

[51] Int. Cl.³ .................. C07C 121/78; C07C 85/11; C07C 85/12
[52] U.S. Cl. .............................. 260/465 E; 260/409; 546/181; 560/19; 560/105; 560/231; 564/385; 564/415; 564/416; 564/417; 564/492; 564/493; 564/494; 260/245.81; 260/245.82; 260/245.86

[58] Field of Search ............... 564/385, 416, 417, 493, 564/494, 415, 492; 260/314, 314.5, 465 E, 409; 546/181; 560/19, 105

[56] References Cited
U.S. PATENT DOCUMENTS
4,256,670 3/1981 Romeier .............................. 564/416

Primary Examiner—Dolph H. Torrence
Attorney, Agent, or Firm—Browdy and Neimark

[57] ABSTRACT

Selective reduction of compounds containing reducible nitro-, nitroso-, nitrilo-, oximes or double bonds is effected by the use of a metal macrocyclic compound in prereduced form, such as a metal phthalocyanine or a metal porphyrin.

10 Claims, No Drawings

METHOD FOR REDUCTION OF REDUCIBLE GROUPS

The invention concerns a method for reduction of reducible groups which contain C atoms or N atoms or a combination of these, especially nitro-, nitroso-, nitrilo-groups, oximes and double bonds and which is selectively executable preserving sensitive, reducible groupings, as well as applications of the method.

Method for reduction of nitro bonds, nitriles and C=C double bonds are known from the following literature, for example:

1. Reduction of nitro compounds to primary amines
   1.1. T. Neilson, et al.: *J. Chem. Soc.* 1962, p. 371 "Pd-catalyzed Reduction of Nitro and Nitroso Bonds to Primary Amines with NaBH$_4$"
   1.2. T. Satoh, S. Suzuki: *Tetrahedron Lett.* 1969, p. 4555. "Reduction of Nitriles, Amides and Nitro Bonds to Primary Amines with NaBH$_4$ and excess CoCl$_2$"
   1.3. K. Hanaya, N. Fujita, H. Kado: *Chem. Ind.*, 1973, p. 794 "Reduction of Aromatic Nitro Bonds to Primary Amines with NaBH$_4$, and [$\phi_3$P]$_2$ NiX$_2$, X=Cl, Br, J"
   1.4. Y. Maki, A. Suguyama, K. Kikuchi, S. Seto: *Chem. Lett.*, 1975, p. 1093. "Reduction of Nitro Bonds to Amines, Hydroxylamine, Azo Bonds, Azoxy Bonds with NaBH$_4$ and Thiols"
   1.5. H. J. Barber, E. Lunt; *J. Chem. Soc.*, 1960, p. 1187. "Reduction of Nitro Bonds to Primary Amines, Secondary Amines, Hydroxylamines, etc. with LiAlH$_4$"
   1.6. Y. Ohgo, S. Takeuchi, J. Yoshimura: *Bull. Chem. Soc. Japan* 44, 282 (1971), U.S. Pat. No. 4,020,108. "Reduction of Nitro Bonds with Cobaloxim/NaBH$_4$"

2. Reduction of nitriles to primary amines
   2.1. R. A. Egli: *Helv. Chim. Acta*, 53, 1970, p. 47. "Raney Ni- and Co-Catalyzed Reduction of Nitriles to Primary Amines with NaBH$_4$ in MeOH/H$_2$O"
   2.2. E. Schenker in *Neuere Methoden der prap. org. Chemie*, Vol. IV, p. 209, Verlag Chemie, Weinheim 1966. "Reduction of Nitriles to Amines with NaBH$_4$ and AlCl$_3$"
   2.3. See 1.2
   2.4. F. E. Gould et al.: *J. Org. Chem.*, 25, 1960, p. 1658; 26, 1961, p. 2602. "Reduction of Nitriles to Primary Amines by Low-Pressure Hydrogenation with H$_2$ on Raney Ni."
   2.5 H. C. Brown, B. C. Subba Rao: *J. Am. Chem. Soc.*, 82, 1960, p. 681. "Reduction of Nitriles to Primary Amines with LiAlH$_4$"

3. Reduction of C=C Double Bonds
   3.1. H. C. Brown, K. Murry: *J. Am. Chem. Soc.*, 81, 1959, p. 4108. "Reduction of Olefins with Diborane"
   3.2. R. W. Bott et al.: *Proc. Chem. Soc.* 1962, p. 337. "Pd-Catalyzed Hydrogenation of Olefins with H$_2$"
   3.3. H. Kropf in *Katalyse an Phthalocyanimen* (Symposium in Hamburg, 1972), Thieme Verlag, Stuttgart, 1973. "High-Temperature Hydrogenation with H$_2$ in the Gas Phase of $\alpha,\beta$ Unsaturated Carbonyl Compounds to Saturated Carbonyl Compounds and to Saturated Alcohols, Catalyzed by NiPc or CoPc."
   3.4. A. Fischli, D. Süss: *Helv. Chim. Acta*, 62, 48, 1979, p. 2361. "Enantio selective Hydrogenations of Conjugate and Isolated C=C Double Bonds by Means of Zinc in Acid, Catalyzed by Vitamin B$_{12}$."
   3.5. M. N. Ricroch, A. Gaudemer: *J. Organomet. Chem*, 67, 1974, p. 119. "Nonstereospecific Hydrogenation of C=C Bonds in $\alpha,\beta$ Unsaturated Carboxylic Acid Esters by Means of H$_2$ or NaBH$_4$, Catalyzed by Vitamin B$_{12}$ or Cobaloxime"
   3.6. R. Miyagawa, T. Yamaguchi: *Nippon Kagaku Kaishi*, 1978, p. 160. "Selective Hydrogenation of Cyclopentadiene to Cyclopentene by means of H$_2$, Catalyzed by (Pyridine)Cobaloxime (II)."

The previously known mehods for reduction of nitro compounds exhibit various drawbacks. For instance, the method expounded in 1.1. is relatively expensive due to the use of precious-metal catalysts and the simultaneous attack on labile groupings—it amounts to dehalogenation of aryl halide as well as hydrogenation of C double bonds—nonselectively. The method described in 1.2. requires large excesses of cobalt salts which causes handling and other difficulties. With other previously known methods for reducing nitro compounds one gets mixtures of primary and higher amines but also of reduced intermediates, etc.

The reduction of nitriles to primary amines by previously known methods is likewise handicapped by frequent lack of selectivity and other problems. In a method described by Fischli in *Helvetica Chimica Acta*, Vol. 61,7 (1978), p. 2560 ff., the nitrile reduction occurs only in an acid medium, and that is why unstable systems can not be reduced under these conditions. Secondary reaction and lack of selectivity at times are also indicated.

As regards the reduction of C=C double bonds, a few methods using metal macrocyclics have already been indicated. These are nonselective at times because of violent reaction conditions or can be carried out (especially when vitamin B$_{12}$ is used) only in acidic pH ranges using expensive compounds.

The basis of the invention is the problem of finding a method of the type named at the beginning. With this method it is possible, in particular, to make, purposefully and exclusively, nitro, nitroso or oxime groupings into primary amino groups without forming secondary amines, hydroxylamines and coupling products and, preserving other functional groups such as aromatics, aromatic halogen, carbonyl groups, C double bonds (also, if necessary, in conjugate form), nitriles and isonitriles, phenols and CH azide compounds. This problem is to be solved in particular using inexpensive, fast-working systems whereby, in accordance with a subfeature, the reduction of nitro or nitroso groups, C=C double bonds present at the same time or CN groupings to primary amino groups or C—C single bonds selectively and without formation of secondary amines, coupling products, etc., is to be accomplished at the same time. Finally, the selective reduction of cyano groups and C=C double bonds (so far as nitro or nitroso groups are not present), preserving other functional groups such as aromatics, aromatic halide carbonyl groups such as carboxylate, carboxylic acid ester, carboxylic acid amides, phenols, CH azide compounds and malonic ester functions is also taken into consideration. Moreover, the selective reduction method is easily controlable and executable, if desired, in protic solvents with water but also in the presence of organic (Co) solvents at neutral pH values or in the alkaline range.

This problem is solved by a method of the kind described at the outset, which is characterized by the fact that for optional selective reduction of the NO$_2$, NO or oxime groups one uses a metal macrocyclic in prereduced form, with an altogether delocalized $\pi$ electron system which exhibits a relative nucleophilia of $n_{CH_3J} \geq 8$ and tetracoordinating metal (ion) with ligands which exhibit N and possibly O or S atoms as coordination points, the ligand or arrangement of ligands being essentially planar; or for optional selective reduction of the $NO_2$, NO, oxime groups and/or a double bond a combination of the metal macrocyclic is employed with an additional reducing agent, where the metal macrocyclic of the general formula

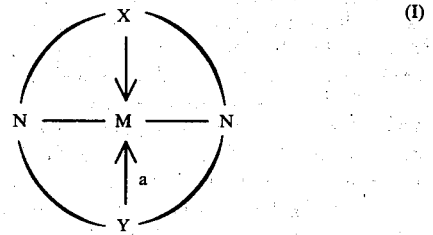

suffices, in which X, Y=N,O and/or S and N=N represent coordination points of one or several ligands, X, Y and N are arranged essentially in a plane and the ligands containing the coordination points X, Y and N may or may not be connected with one another, the metal (ion) being connected with the coordination points of the ligand or ligands by atomic or coordinative bond a.

The metal macrocyclics usable in the method of the invention can be determined on the basis of their relative nucleophilia on the Pearson scale (R. G. Pearson, H. Sobel, J. Songstad: *J. Am. Chem. Soc.*, 90, 1968 p. 319) where they are to exhibit a value of $n_{CH_3J} \geq 8$ and preferably $\geq 10$. In addition, the suitability of the metal macrocyclics of coordinated metal as metal ion, which is at least "incontact" with two N coordination points of the ligand and alternatively with two N,O or S coordination points of the same or different ligands can be established by a simple reaction.

Metal macrocyclics suitable for the method can be determined according to the following prescription:

In 3 centrifuge tubes (volume 20 ml, diameter 1 cm) which are sealed with paraffin one mixes in each 15 ml ethanol Solution A: 100 mg metal macrocyclic Solution B: 300 mg sodium borohydride, 100 mg metal macrocyclic solution C: 300 mg sodium borohydride, 100 mg metal macrocyclic and, after the color change as in solution B has taken place, 2 ml nitrobenzene, cooling it to room temperature if necessary.

The 3 solutions are centrifuged (which is done after the occurrence of the color change in solution C or, if the latter is not perceptible, after 48 hours), and the colors of solutions A, B and C are compared visually or by means of a photometer. Suitable for the method are metal macrocycles whose solutions meet the following criteria:

(1) Colors of solutions A and B are different, (2) Colors of solutions B and C are different or color of solution B is present only weakly in solution C, [Colors of solutions A and C may be the same (ideal case). The intensity of the colors of solution A is very low; that of solution B is very high; that of solution C is weak compared to that of solution B or very low (like solution A, ideal case)].

The prescription given above is likewise suitable, in an analogous manner, for determining the reactivity of one metal macrocyclic relative to the other functional groups taken into consideration.

Metal macrocyclics are universally known, and for the purposes of the invention reference is made, by way of example, to the following bibliography.

4. Metal Macrocyclics 4.1. F. H. Moser, A. L. Thomas: *Phthalocyanine Compounds*, Reinhold Publishing Corp., New York, 1963. "Survey of Metal Phthalocyanines (Also Halogenated)," patent literature.

4.2. A. B. P. Lever: *Adv. Inorg. Chem. Radiochem.*, 7, (1965), p. 27 "Survey of Metal Phthalocyanines and Their Chemistry".

4.3. K. M. Smith: *Porphyrins and Metalloporphysins*, Elsevier Scientific Publ. Co., Amsterdam, 1975. "Survey of Metalloporphyrins"

4.4. A. Giraudeau, I. Ezahr, M. Gross, H. J. Callot, J. Jordan: *Bioelectrochem. Bioenergetics*, 3, (1976), p. 519. "Tetra Phenylporphyrins Substituted with 1–4 CN groups"

4.5. N. A. Kolesnikov, V. F. Borodkin: *Izv. Vapsh Ucheb. Zaved. Khim. Tekhnol.*, 1972, p. 880. "Preparation of Bis-[2-(1'-imino-3'-isoindolenin)-5-amino-1,3,4-thiadiazolato]-cobalt (II)"

Among the metal macrocycles known previously, those particularly suited to the purposes of the invention can be selected quite simply on the basis of:

(a) the positive finding of the reaction given above, (b) the exceeding of the relative nucleophilia, and (c) the indicated tetracoordination of the central metal (ion) which is held by the indicated ligand(s) in an essentially planar configuration.

Preferred metal macrocyclics fulfill conditions (a) to (c) above, it being particularly advantageous if at least one of the heteroatoms of the tetracoordinating ligands is formally linked only coordinatively (i.e. without an atomic bond).

The metals of the macrocyclic generally exhibit d-orbitals to particular advantage and come preferably from the first transition period of the periodic table, and it is advantageous if they are Fe, Co, Ni, Mn, Ti, V, Cr or Mo, in ionic state if necessary.

However, within the scope of the invention metals of the main groups, such as Al, Mg, Sn for example, may also be included in the macrocyclic.

Systems preferred within the framework of the invention are the following:

(a) metal phthalocyanine, particularly of the general formula (II)

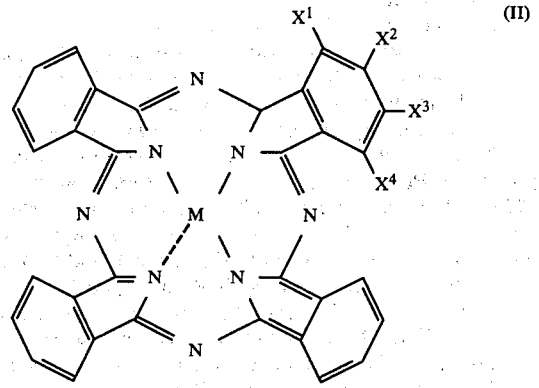

in which $x^{1-4}$ represent H, halogens such as Cl, F, cyano or possibly other substituents with -I- effect and which can replace one or several of the benzenoid rings, (b) a metal porphyrin of the general formula (III)

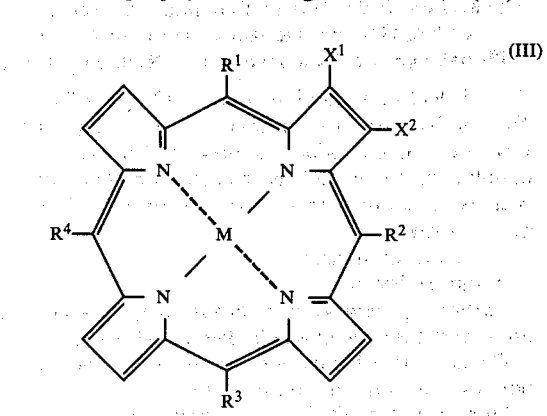

in which $R^1$ to $R^4$ represent H, phenyl or low alkyl and $X^1$, $X^2$ signify H, halogen, chlorine, bromine, cyano or an -I- substituent, or (c) a mixed cyclic of the general formula (IV)

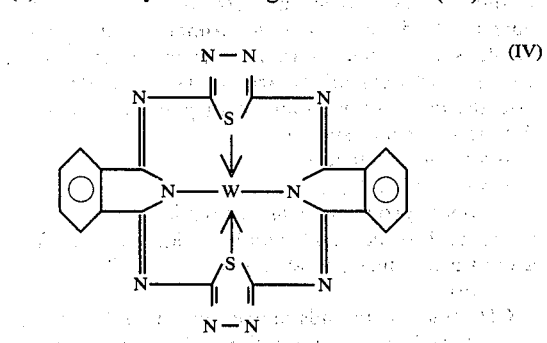

which can, if necessary, be substituted in the benzenoid with halogens, cyano and other -I- substituents.

Metal macrocyclics particularly preferred in the method according to the invention are Co (II) phthalocyanine complexes, optionally in prereduced form. In addition, the complexes of manganese (II), chromium (II), iron (II), molybdenum (II), nickel (II), oxyvanadium (IV), titanyl (IV) phthalocyanine are given particularly preferential consideration. Another system especially favorable in the framework of the invention is bis[2-(1'-imino-3'-isoindolenin)-5-amino-1,3,4-thiadiazolato]cobalt (II).

Within the framework of the method according to the invention, two principal variants are distinguished. In one variant, with regard to the nitro or nitroso compound to be reduced, an approximately equivalent or excess amount of charged metal macrocyclic is used which was prereduced in a previous reaction. Prereduction can be carried out with sodium boranate, lithium alanate, in some cases with hydrazine, but sometimes also with H$_2$, etc. Prereduction generally reduces the degree of oxidation of the metal by one or two valence numbers. Prereduction can be accomplished in a manner analogous to or identical to the one described, for example, in Justus Liebig's *Annalen der Chemie* (Annals of Chemistry), 1979, p. 287. The complex here develops in anionic form.

The use of the prereduced macrocyclic leads to a selective reduction of nitro and nitroso compounds while preserving labile groups such as double bonds, nitrile groups, aromatic or hetrocyclically linked halogens, etc., as is shown below for example, in tabular form by means of the preferred metal macrocyclic cobalt (II)-phthalocyanine anion.

The alternative way of carrying out the method according to the invention consists of employing the metal macrocyclic in the presence of an additional reducing agent. In this form of execution of the method of the invention catalytic quantities of the metal macrocyclic are sufficient as a rule, and approximately equivalent amounts, or more, of the "conventional" reducing agent employed similarly are consumed. As reducing agents used besides the catalytic quantity of metal macrocyclic, the following can be mentioned by way of example: sodium boranate, lithium alanate or derivatives of these, particularly their reaction products with alcohols, but also hydrogen. Particularly preferred is sodium boranate, especially since when a sodium-boranate-containing combination is used, the work can be done in protic solvents including water. If the combination consisting of metal macrocyclic and reducing agent is used, it is not necessary to reduce the metal macrocyclic in a previous, separate reaction. When the combination consisting of metal macrocyclic with an additional reducing agent is used nitriles and C═C double bonds can also be reduced to primary amine or C—C single bonds. For this reason, the use of this combination is desirable whenever either nitrilo groups or double bonds alone are to be reduced or a combination of these or possibly simultaneously together with existing nitro or nitroso groups.

Normally, the reaction takes place under protective gas or under the shield of the gas produced by the reaction. As long as lithium alanate is also used as the conventional reducing agent, the use of protic solvents with the inclusion of water is a possibility. As cosolvents, all solvents except alkyl halides and nitro hydrocarbons (as well as ketones in NaBH$_4$ reductions) are possibilities.

The reaction, including working up the reaction mixture, can be carried out to advantage in neutral ranges and especially in a pH range of 7 to 10 (preferably 7 to 9). Supervision of the reaction process is very well possible by dosing the reducing agent.

Within the framework of the method of the invention, the use of cobalt (II) phthalocyanine, either alone or in combination with sodium boranate, is particularly preferable. If a metal macrocyclic is designated within the framework of the method of the invention for reduction with hydrogen gas, it is particularly advantageous to work in a low temperature range, for example, 0° to 80° C. but especially 10°–40° C. By the use of metal macrocyclics, and in particular the preferred ones indicated above, selective hydrogenation with hydrogen gas can be accomplished very rapidly even at normal pressure.

The reduction of nitriles by the combination of a metal macrocyclic with an additional reducing agent such as sodium boranate, for example, can be carried out in the neutral or alkaline pH range. The reduction of double bonds is carried out to particular advantage with a combination of metal phthalocyanines and a reducing agent selected from among sodium boranate, lithium alanate or its alcoholates in a solvent or in the presence of hydrogen, at a low temperature.

The method according to the invention is suited to the synthesis of compounds in which, beginning with nitro or nitroso groupings or also other stages of oxidation, the selective formation of primary amines is achieved. However, it is also suitable for production of compounds whose starting products contain no nitro or nitroso compounds or other intermediates but with which a selective reduction of the nitrilo groups or the double bond is achieved. Finally, optional reduction of nitroso groups together with double bonds, even ones in a activated form such as nitrilo groups but also with the elimination of the reduction of the two last-named substituents, can be carried out by applying the method of the invention. By this means it is simple, in particular, to synthesize pharmaceutical systems, herbicides and insecticides in the production of which there are, besides other reduction-sensitive groups, amino groups in the final product. Thus, for instance, the reduction of heterocyclically linked nitro groups is also possible without simultaneously removing heterocyclically linked halogen, etc. The method is also suitable for producing heterocyclics, e.g. by a "stew" method. This can be done, for instance via reduction of formyl-substituted systems with nitro-substituted systems which may, if necessary, be connected to the same nucleus, since the reduction does yield the amino group but leaves the aldehyde function untouched depending on the reaction conditions so that reduction and condensation can be achieved with formation of an aromatic (but also partially saturated, if desired) system.

Below, the invention is explained on the basis of the system preferred according to the invention, cobalt (I)-phthalocyanine-anion, optionally in combination with reducing agents such as sodium boranate. In addition, however, other typical representatives are also included, these standing for other metal macrocyclics which are possibilities within the framework of the invention [Pc=phthalocyanine].

Method for Reduction of Functional Compounds by Cobalt (I)-Phthalocyanine-Anion or Cobalt Phthalocyanine Catalyzed with a Reducing Agent (1) Selective reduction with [PcCo$^I$] $^\ominus$ of only the NO$_2$ or NO group to primary amino groups without formation of secondary amines, hydroxylamines and coupling products such as azo azoxy and hydrazo compounds, in addition to and preserving other functional groups such as Aromatic substances,
Aromatic halide,
Carbonyl groups such as carboxylate, carboxylic acid ester, carboxylic acid amide, ketone, aldehyde,
C=C double bonds, also conjugate carbonyl compounds and those unsaturated in $\alpha$, $\beta$,
Nitriles and isonitriles (also conjugate),
Phenols,
CH azide compounds such as malonic and acetoacetic ester functions.

(2) Selective, PcCo-catalyzed reduction with NaBH$_4$ of the NO$_2$, NO, oxime and CN group as well as conjugate C=C double bonds to primary amino group or C—C single bond without formation of secondary amines, hydroxylamines, azo, azoxy and hydrazo compounds, in addition to and with preservation of other functional groups such as Aromatic substances
Aromatic halide,
Carbonyl groups such as carboxylate, carboxylic acid ester, carboxylic acid amide, (aldehyde or ketone groups are reduced to alcohols)
Phenols
CH azide compounds such as malonic ester functions.

(3) Simultaneous reduction of various functional groups with preservation of third functional groups in a compound with NaBH$_4$, PcCo-catalyzed, see Table 1 and Table 4.

TABLE 1

Selectivity of the reductions of functional organic compounds with cobalt (I)-phthalocyanine anion or NaBH$_4$/PcCo catalytic

| Educts | [PcCo$^I$]$^\ominus$ | NaBH$_4$*/PcCo catalyst |
|---|---|---|
| NO$_2$ aromatic and aliphatic | NH$_2$ | NH$_2$ |
| NO | NH$_2$ | NH$_2$ |
| CN | CN | NH$_2$ |
| \>C=C< | \>C=C< | —+—+— |
| =N—OH | — | NH$_2$ |
| NO$_2$/\>C=C< | NH$_2$/\>C=C< | NH$_2$/ —+—+— |
| NO$_2$/C=O | NH$_2$/C=O | NH$_2$/CH$_2$—OH |
| NO$_2$/C(=O)OR | NH$_2$/C(=O)OR | NH$_2$/C(=O)OR |
| NO$_2$/CN | NH$_2$/CN | NH$_2$/NH$_2$ |
| CN/\>C=C< | CN/\>C=C< | NH$_2$/ —+—+— |

TABLE 1-continued
Selectivity of the reductions of functional organic compounds with cobalt (I)-phthalocyanine anion or NaBH₄/PcCo catalytic

| Educts | Products after reaction with | |
|---|---|---|
| | [PcCo$^I$]$^\ominus$ | NaBH$_4$*/PcCo catalyst |
| =/C=O | =/C=O | —+—+—/CH$_2$—OH |
| NO$_2$/C(=O)(OR) konj. | NH$_2$/C(=O)(OR) | NH$_2$/C(=O)(OR) / —+—+— |
| NO$_2$/C(=O)(OR)(NHR) /C(=O)/OR | — | NH$_2$/C(=O)(OR) /C(=O)(NHR) |
| NO$_2$/—NC | NH$_2$/—NC | /OR |

*In some cases replaceable by Na amalgam and other reducing agents

TABLE 2
PcCo—catalyzed reduction by means of NaBH₄ of nitro compounds in approximately 0.2 m[sic] solution of ETOH at 20° C.

| Nitro compound | Molar proportion NaBH₄/Nitro Comp. | Molar proportion PcCo/Nitro Comp. | Agitation time [h] | Primary Amine | Yield in primary amine [%] |
|---|---|---|---|---|---|
| p-NO$_2$—C$_6$H$_4$—CH$_3$ | 7.5 | 8.1 | 2 | p-NH$_2$—C$_6$H$_4$—CH$_3$ | 51 |
| " | 7.5 | 0.1 | 21 | " | 83 |
| " | 7.5 | 0.1 | 72 | " | 88 |
| p-NO$_2$—C$_6$H$_4$—Cl | 7.5 | 0.1 | 2 | p-NH$_2$—C$_6$H$_4$—Cl | 60 |
| " | 7.5 | 0.1 | 168 | " | 83 |
| " | 2 | 0.1 | 71 | " | 74 |
| " | 7.5 | 0.01 | 3 | " | 26 |
| " | 7.5 | 0.01 | 70 | " | 76 |

TABLE 3
Reduction of functional organic compounds by means of [PcCo$^I$]$^{(-)}$ in MeOH at 20° C.

| Educt | Agitation time [h] | Product | Yield (%) |
|---|---|---|---|
| 1-Nitronaphthalene | 48 | 1-Naphthylamine | 70 |
| NO$_2$—n-C$_3$H$_7$ | 95 | NH$_2$—n-C$_3$H$_7$ | 66 |
| NC—(CH$_2$)$_4$—CN$^{(a)}$ | 285 | NC—(CH$_2$)$_4$—CN | 99 |
| C$_6$H$_5$—CH=CH—CO$_2$ET$^{(b)}$ | 340 | C$_6$H$_5$—CH=CH—CO$_2$Me | 99 |
| p-NO$_2$—C$_6$H$_4$—CH$_2$—CN | 62 | p-NH$_2$—C$_6$H$_4$—CH$_2$—CN | 95 |
| p-NO$_2$—C$_6$H$_4$—CH=CH—CO$_2$ET$^{(c)}$ | 65 | p-NH$_2$—C$_6$H$_4$—CH=CH—CO$_2$ET | 82 |
| m-NO$_2$—C$_6$H$_4$—C(=O)H | 45 | m-NH$_2$—C$_6$H$_4$—C(=O)H | 53 |
| p-NO$_2$—C$_6$H$_4$—C(=O)—CH$_3$ | 90 | p-NH$_2$—C$_6$H$_4$—C(=O)—CH$_3$ | 78 |
| o-NO$_2$—C$_6$H$_4$—C(=O)H | 90 | o-NH$_2$—C$_6$H$_4$—C(=O)H | 96 |
| p-NO$_2$—C$_6$H$_4$—NC | 72 | p-NH$_2$—C$_6$H$_4$—NC | 76 |

Synthesis of heterocyclic compounds

TABLE 3-continued

Reduction of functional organic compounds by means of [PcCo$^I$]$^{(-)}$ in MeOH at 20° C.

| Educt | Agitation time [h] | Product | Yield (%) |
|---|---|---|---|
| o-NO$_2$—C$_6$H$_4$—C(=O)H + CH$_3$—C(=O)—CH$_3$ | 63 | 2-methyl quinoline | 77 |

[a] no reaction
[b] quantitative ester interchange
[c] EtOH as reaction medium

TABLE 4

PcCo-catalyzed reduction of functional organic compounds by means of NaBH$_4$ in EtOH at 20° C.

| Educt | Agitation time [h] | Product | Yield [%] |
|---|---|---|---|
| p-NO$_2$—C$_6$H$_4$—CH$_3$ | 21–72 | p-NH$_2$—C$_6$H$_5$—CH$_3$ | 83–88 |
| p-NO$_2$—C$_6$H$_4$—Cl | 168 | p-NH$_2$—C$_6$H$_4$—Cl | 83 |
| NO$_2$—n-C$_3$H$_7$ | 189 | NH$_2$—n-C$_3$H$_7$ | 76 |
| p-NO—C$_6$H$_4$—Cl | 94 | p-NH$_2$—C$_6$H$_4$—Cl | 95 |
| C$_6$H$_5$—CN | 168 | C$_6$H$_5$—CH$_2$—NH$_2$ | 53 |
| C$_6$H$_5$—CH$_2$—CN | 168 | C$_6$H$_5$—CH$_2$—CH$_2$—NH$_2$ | 11 |
| NC—(CH$_2$)$_4$—CN | 188 | NH$_2$—(CH$_2$)$_6$—NH$_2$ | 27 |
| C$_6$H$_5$—CH$_2$—CONH$_2$[a] | 24 | C$_6$H$_5$—CH$_2$—CONH$_2$ | 67 |
| C$_6$H$_5$—CH=CH—CO$_2$Et | 167 | C$_6$H$_5$—CH$_2$—CH$_2$—CO$_2$Et | 92 |
| CH$_3$—CH=CH—CO$_2$Et | 284 | CH$_3$—CH$_2$—CH$_2$—CO$_2$Et | 69 |
| p-NO$_2$—C$_6$H$_4$—NH$_2$ | 120 | p-NH$_2$—C$_6$H$_4$—NH$_2$ | 33 |
| p-NO$_2$—C$_6$H$_4$—OH | 117 | p-NH$_2$—C$_6$H$_4$—OH | 84 |
| p-NO$_2$—C$_6$H$_4$—CH$_2$—CN | 141 | p-NH$_2$—C$_6$H$_4$—CH$_2$—CH$_2$—NH$_2$ | 46 |
| 2,4-Dinitrochlorobenzene | 214 | Chlorophenylenediamine(2,4) | 79 |
| p-NO$_2$—C$_6$H$_4$—CH=CH—CO$_2$Et | 120 | p-NH$_2$—C$_6$H$_4$—CH$_2$—CH$_2$—CO$_2$Et | 64 |
| p-NO$_2$—C$_6$H$_4$—C(=O)—CH$_3$ | 48 | p-NH$_2$—C$_6$H$_4$—CH(OH)—CH$_3$ | 79 |
| 4-NHCOCH$_3$, 2-OCH$_3$, 5-CO$_2$CH$_3$ nitrobenzene (O$_2$N-) | 2,5 | 4-NHCOCH$_3$, 2-OCH$_3$, 5-CO$_2$CH$_3$ aniline (H$_2$N-) | 93 |
| 4-NH$_2$, 2-OCH$_3$, 5-CO$_2$CH$_3$ nitrobenzene (O$_2$N-) | 94 | 4-NH$_2$, 2-OCH$_3$, 5-CO$_2$CH$_3$ aniline (H$_2$N-) | 84 |
| CH$_3$—CH=CH—CN | 166 | CH$_3$—CH$_2$—CH$_2$—CH$_2$—NH$_2$ | 36 |
| NC—CH$_2$—CO$_2$Et | 311 | HN—CH$_2$—CH$_2$—C=O, O=C—CH$_2$—CH$_2$—NH (cyclic) | 21 |
| C$_6$H$_5$—CH=CH—C(=O)H | 70 | C$_6$H$_5$—CH$_2$—CH$_2$—CH$_2$—OH | 96 |
| CH$_3$—(CH$_2$)$_7$—CH=CH—(CH$_2$)$_7$—CO$_2$H | 93 | CH$_3$—(CH$_2$)$_{16}$—CO$_2$H[b] | 42[b] |

[a] no reaction  [b] in addition to 46% oleic acid (initial product)

TABLE 5

Reduction of nitro compounds by means of [Fe °Pc]$^{2-}$ in EtOH at 20° C.

| Educt | Agitation time [h] | Product | Yield [%] |
|---|---|---|---|
| p-NO$_2$—C$_6$H$_4$—CH$_3$ | 1 | p-NH$_2$—C$_6$H$_4$—CH$_3$ | 78 |

TABLE 1-continued
Selectivity of the reductions of functional organic compounds with cobalt (I)-phthalocyanine anion or $NaBH_4/PcCo$ catalytic

| Educts | Products after reaction with | |
|---|---|---|
| | $[PcCo^I]^{\ominus}$ | $NaBH_4^*/PcCo$ catalyst |
| $=/C=O$ | $=/C=O$ | $+$ $+$ $/CH_2-OH$ |
| $NO_2/C(=O)(OR)$ konj. | $NH_2/C(=O)(OR)$ | $NH_2/C(=O)(OR)$ $/$ $+$ $+$ |
| $NO_2/C(=O)(OR)$ $/C(=O)(NHR)$ $/OR$ | — | $NH_2/C(=O)(OR)$ $/C(=O)(NHR)$ |
| $NO_2/-NC$ | $NH_2/-NC$ | $/OR$ |

*In some cases replaceable by Na amalgam and other reducing agents

TABLE 2
PcCo—catalyzed reduction by means of $NaBH_4$ of nitro compounds in approximately 0.2 m[sic] solution of ETOH at 20° C.

| Nitro compound | Molar proportion $NaBH_4$ / Nitro Comp. | Molar proportion PcCo / Nitro Comp. | Agitation time [h] | Primary Amine | Yield in primary amine [%] |
|---|---|---|---|---|---|
| p-$NO_2$—$C_6H_4$—$CH_3$ | 7.5 | 8.1 | 2 | p-$NH_2$—$C_6H_4$—$CH_3$ | 51 |
| " | 7.5 | 0.1 | 21 | " | 83 |
| " | 7.5 | 0.1 | 72 | " | 88 |
| p-$NO_2$—$C_6H_4$—Cl | 7.5 | 0.1 | 2 | p-$NH_2$—$C_6H_4$—Cl | 60 |
| " | 7.5 | 0.1 | 168 | " | 83 |
| " | 2 | 0.1 | 71 | " | 74 |
| " | 7.5 | 0.01 | 3 | " | 26 |
| " | 7.5 | 0.01 | 70 | " | 76 |

TABLE 3
Reduction of functional organic compounds by means of $[PcCo^I]^{(-)}$ in MeOH at 20° C.

| Educt | Agitation time [h] | Product | Yield (%) |
|---|---|---|---|
| 1-Nitronaphthalene | 48 | 1-Naphthylamine | 70 |
| $NO_2$—n-$C_3H_7$ | 95 | $NH_2$—n-$C_3H_7$ | 66 |
| NC—$(CH_2)_4$—$CN^{(a)}$ | 285 | NC—$(CH_2)_4$—CN | 99 |
| $C_6H_5$—CH=CH—$CO_2ET^{(b)}$ | 340 | $C_6H_5$—CH=CH—$CO_2Me$ | 99 |
| p-$NO_2$—$C_6H_4$—$CH_2$—CN | 62 | p-$NH_2$—$C_6H_4$—$CH_2$—CN | 95 |
| p-$NO_2$—$C_6H_4$—CH=CH—$CO_2ET^{(c)}$ | 65 | p-$NH_2$—$C_6H_4$—CH=CH—$CO_2ET$ | 82 |
| m-$NO_2$—$C_6H_4$—C(=O)H | 45 | m-$NH_2$—$C_6H_4$—C(=O)H | 53 |
| p-$NO_2$—$C_6H_4$—C(=O)—$CH_3$ | 90 | p-$NH_2$—$C_6H_4$—C(=O)—$CH_3$ | 78 |
| o-$NO_2$—$C_6H_4$—C(=O)H | 90 | o-$NH_2$—$C_6H_4$—C(=O)H | 96 |
| p-$NO_2$—$C_6H_4$—NC | 72 | p-$NH_2$—$C_6H_4$—NC | 76 |

Synthesis of heterocyclic compounds

TABLE 3-continued

Reduction of functional organic compounds by means of [PcCo$^I$]$^{(-)}$ in MeOH at 20° C.

| Educt | Agitation time [h] | Product | Yield (%) |
|---|---|---|---|
| o-NO$_2$—C$_6$H$_4$—CHO + CH$_3$—CO—CH$_3$ | 63 | 2-methyl quinoline | 77 |

[a] no reaction
[b] quantitative ester interchange
[c] EtOH as reaction medium

TABLE 4

PcCo-catalyzed reduction of functional organic compounds by means of NaBH$_4$ in EtOH at 20° C.

| Educt | Agitation time [h] | Product | Yield [%] |
|---|---|---|---|
| p-NO$_2$—C$_6$H$_4$—CH$_3$ | 21-72 | p-NH$_2$—C$_6$H$_5$—CH$_3$ | 83-88 |
| p-NO$_2$—C$_6$H$_4$—Cl | 168 | p-NH$_2$—C$_6$H$_4$—Cl | 83 |
| NO$_2$—n-C$_3$H$_7$ | 189 | NH$_2$—n-C$_3$H$_7$ | 76 |
| p-NO—C$_6$H$_4$—Cl | 94 | p-NH$_2$—C$_6$H$_4$—Cl | 95 |
| C$_6$H$_5$—CN | 168 | C$_6$H$_5$—CH$_2$—NH$_2$ | 53 |
| C$_6$H$_5$—CH$_2$—CN | 168 | C$_6$H$_5$—CH$_2$—CH$_2$—NH$_2$ | 11 |
| NC—(CH$_2$)$_4$—CN | 188 | NH$_2$—(CH$_2$)$_6$—NH$_2$ | 27 |
| C$_6$H$_5$—CH$_2$—CONH$_2$[a] | 24 | C$_6$H$_5$—CH$_2$—CONH$_2$ | 67 |
| C$_6$H$_5$—CH=CH—CO$_2$Et | 167 | C$_6$H$_5$—CH$_2$—CH$_2$—CO$_2$Et | 92 |
| CH$_3$—CH=CH—CO$_2$Et | 284 | CH$_3$—CH$_2$—CH$_2$—CO$_2$Et | 69 |
| p-NO$_2$—C$_6$H$_4$—NH$_2$ | 120 | p-NH$_2$—C$_6$H$_4$—NH$_2$ | 33 |
| p-NO$_2$—C$_6$H$_4$—OH | 117 | p-NH$_2$—C$_6$H$_4$—OH | 84 |
| p-NO$_2$—C$_6$H$_4$—CH$_2$—CN | 141 | p-NH$_2$—C$_6$H$_4$—CH$_2$—CH$_2$—NH$_2$ | 46 |
| 2,4-Dinitrochlorobenzene | 214 | Chlorophenylenediamine(2,4) | 79 |
| p-NO$_2$—C$_6$H$_4$—CH=CH—CO$_2$Et | 120 | p-NH$_2$—C$_6$H$_4$—CH$_2$—CH$_2$—CO$_2$Et | 64 |
| p-NO$_2$—C$_6$H$_4$—CO—CH$_3$ | 48 | p-NH$_2$—C$_6$H$_4$—CH(OH)—CH$_3$ | 79 |
| O$_2$N—C$_6$H$_3$(NH—CO—CH$_3$)(O—CH$_3$)(CO$_2$—CH$_3$) | 2,5 | H$_2$N—C$_6$H$_3$(NH—CO—CH$_3$)(O—CH$_3$)(CO$_2$—CH$_3$) | 93 |
| O$_2$N—C$_6$H$_3$(NH$_2$)(O—CH$_3$)(CO$_2$—CH$_3$) | 94 | H$_2$N—C$_6$H$_3$(NH$_2$)(O—CH$_3$)(CO$_2$—CH$_3$) | 84 |
| CH$_3$—CH=CH—CN | 166 | CH$_3$—CH$_2$—CH$_2$—CH$_2$—NH$_2$ | 36 |
| NC—CH$_2$—CO$_2$Et | 311 | HN—CH$_2$—CH$_2$—C(=O)—O=C—CH$_2$—CH$_2$—NH (cyclic) | 21 |
| C$_6$H$_5$—CH=CH—CHO | 70 | C$_6$H$_5$—CH$_2$—CH$_2$—CH$_2$—OH | 96 |
| CH$_3$—(CH$_2$)$_7$—CH=CH—(CH$_2$)$_7$—CO$_2$H | 93 | CH$_3$—(CH$_2$)$_{16}$—CO$_2$H[b] | 42[b] |

[a] no reaction
[b] in addition to 46% oleic acid (initial product)

TABLE 5

Reduction of nitro compounds by means of [Fe °Pc]$^{2-}$ in EtOH at 20° C.

| Educt | Agitation time [h] | Product | Yield [%] |
|---|---|---|---|
| p-NO$_2$—C$_6$H$_4$—CH$_3$ | 1 | p-NH$_2$—C$_6$H$_4$—CH$_3$ | 78 |

TABLE 5-continued

Reduction of nitro compounds by means of [Fe °Pc]$^{2-}$ in EtOH at 20° C.

| Educt | Agitation time [h] | Product | Yield [%] |
|---|---|---|---|
| p-NO$_2$—C$_6$H$_4$—CH=CH—CO$_2$Et | 1 | p-NH$_2$—C$_6$H$_4$—CH=CH—CO$_2$Et | 63 |

TABLE 6.

Metal-macrocyclic-catalyzed reduction of functional organic compounds by means of NaBH$_4$ in EtOH at 20° C.

| Catalyst | Educt | Agitation time [h] | Product | Yield [%] |
|---|---|---|---|---|
| Mn$^{II}$Pc | p-NO$_2$—C$_6$H$_4$—Cl | 91 | p-NH$_2$—C$_6$H$_4$—Cl | 78 |
| Fe$^{II}$Pc | C$_6$H$_5$—CN | 162 | C$_6$H$_5$—NH$_2$ | 19 |
| " | C$_6$H$_5$—CONH$_2$$^c$ | 260 | C$_6$H$_5$—CONH$_2$ | 98 |
| Ni$^{II}$Pc | p-NO$_2$—C$_6$H$_4$—Cl | 70 | p-NH$_2$—C$_6$H$_4$—Cl | 16 |
| Cr$^{II}$Pc | p-NO$_2$—C$_6$H$_4$—Cl | 140 | p-NH$_2$—C$_6$H$_4$—Cl | 83 |
| Mo$^{II}$Pc | p-NO$_2$—C$_6$H$_4$—Cl | 42 | p-NH$_2$—C$_6$H$_4$—Cl | 55 |
| Co—N$_2$—S$_2$—Lig.$^d$ | p-NO$_2$—C$_6$H$_4$—Cl | 92 | p-NH$_2$—C$_6$H$_4$—Cl | 77 |
| V$^{IV}$OPc | p-NO$_2$—C$_6$H$_4$—Cl | 22 | p-NH$_2$—C$_6$H$_4$—Cl | 91 |
| py→(Co$^{III}$)—Cl | C$_6$H$_5$—CH=CH—CO$_2$Et | 1 | C$_6$H$_5$—CH$_2$—CH$_2$—CO$_2$Et | 90 |

$^c$no reaction
$^d$Bis[2-(1'-imino-3'-isoindolenine)-5-amino-1, 3, 4-thiadiazolato]-cobalt (II)

Summary

Reduction of C=O double bonds with NaBH$_4$ catalyzed by metal macrocyclics.

| Catalyst | Educt | Agitation time [h] | Product | Yield [%] | Example No. |
|---|---|---|---|---|---|
| Co$^{II}$Pc | Oleic Acid | 93 | Stearic Acid | 42 | 17 |
| " | CH$_3$—CH=CH—CO$_2$Et | 284 | CH$_3$—CH$_2$—CH$_2$—CO$_2$Et | 69 | 18 |
| " | C$_6$H$_5$—CH=CH—CO$_2$Et | 167 | C$_6$H$_5$—CH$_2$—CH$_2$—CO$_2$Et | 92 | 19 |
| " | p-NO$_2$—C$_6$H$_4$—CH=CH—CO$_2$Et | 120 | p-NH$_2$—C$_6$H$_4$—CH$_2$—CH$_2$—CO$_2$Et | 64 | 24 |
| " | CH$_3$—CH=CH—CN | 166 | CH$_3$—CH$_2$—CH$_2$—CH$_2$—NH$_2$ | 36 | 28 |
| " | 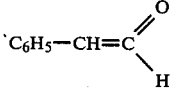 C$_6$H$_5$—CH=C(=O)(H) | 70 | C$_6$H$_5$—CH$_2$—CH$_2$—CH$_2$—OH | 96 | 29 |

The invention is explained further in the illustrative examples below. Unless otherwise indicated, the metal macrocyclics used were synthesized according to the bibliographic citations. The final products formed in the method of the invention were identified in some cases on the basis of micranalyses and in some cases on the basis of the spectra known previously. The yields indicated in the illustrative examples are not optimized.

ILLUSTRATIVE EXAMPLES

Example 1

Under nitrogen, 21.2 g (23.5 mmol) lithium cobalt (I) phthalocyanine×4.5 THF and 310 mg (3.5 mmol) 1-nitropropane are agitated in 100 ml methanol for 95 hours at 20° C. Cooling with ice, the green reaction mixture is mixed with 10 ml 5 N hydrochloric acid and the blue precipitate is centrifuged which is washed out with ethanol. The centrifugate collected is concentrated and the residue is separated into 1 N sodium hydroxide solution and ether. The ether phase is extracted with 10 ml 1 N hydrochloric acid and 10 ml water, and the aqueous extracts are concentrated to dryness, 220 mg (66%) n-propylamine-hydrochloride being left behind.

Example 2

Under nitrogen, 11.5 g (12.7 mmol) lithium cobalt (I) phthalocyanine×4.5 THF and 324 mg (2 mmol) p-nitrobenzyl cyanide are agitated in 60 ml methanol for 62 hours at 20° C. The green reaction mixture is mixed with 10 ml water; then CO$_2$ and air are passed into it for 5 min., and the blue precipitate is centrifuged which is washed out with ethanol. The centrifugate collected is concentrated, and the residue separated into water and ether. After compression of the ether phase, which is dried via sodium sulfate, 250 mg (95%) p-amino benzyl cyanide is obtained.

Example 3

Under nitrogen, 17.5 g (19.4 mmol) lithium-cobalt (I) phthalocyanine×4.5 THF and 663 mg (3 mmol) p-nitro cinnamic ethyl ester are agitated in 100 ml ethanol for 65 hours at 20° C. The green reaction mixture is mixed with 10 ml water; CO$_2$ and air are passed into it for 5 min. and the blue precipitate is centrifuged which is washed out with ethanol and ether. The centrifugate collected is concentrated and the residue separated into methylene chloride and water. Concentration of the organic phase, dried with sodium sulfate, produces 470 mg (82%) p-amino cinnamic ethyl ester.

EXAMPLE 4

Under nitrogen, 12.3 g (13.6 mmol) lithium cobalt (I) phthalocyanine x 4.5 THF and 322 mg (2 mmol) O-nitrobenzaldehyde are agitated in 65 ml methanol for 90 hours at 20° C. The green reaction mixture is mixed with 10 ml water; $CO_2$ and air are passed in for 5 min., and the blue precipitate is centrifuged which is washed with ethanol. The centrifugate collected is concentrated, and the residue separated into ether and water. Concentration of the ether phase, dried with sodium sulfate, produces 230 mg (96%) O-amino benzaldehyde.

EXAMPLE 5

Under nitrogen 11.8 g (13.1 mmol) lithium cobalt (I) phthalocyanine x 4.5 THF, 5 ml acetone and 322 mg (2 mmol) O-nitrobenzaldehyde are agitated for 63 hours at 20° C. The green reaction mixture is mixed with 10 ml water; $CO_2$ and air are passed into it for 5 min., and the blue precipitate is centrifuged which is washed with methanol. The centrifugate collected is concentrated and the residue separated into ether and water. The organic phase is dried with potassium hydroxide and concentrated, and the residue digested with pentane. After concentration of the pentane extracts, 220 mg (77%) 2-methyl guinoline is obtained.

EXAMPLE 6

Under nitrogen, 11.6 g (12.8 mmol) lithium-cobalt (I) phthalocyanine x 4.5 THF and 296 mg (2 mmol) p-nitrophenyl isonitrile are agitated in 65 ml methanol for 72 hours at 20° C. The green reaction mixture is mixed with 5 ml water; $CO_2$ and air are passed in for 5 min., and the blue precipitate is centrifuged which is washed with ethanol. The centrifugate collected is concentrated and the residue separated into ether and water. Concentration of the ether phase, dried with sodium sulfate, produces 180 mg (76%) p-aminophenylisonitrile.

EXAMPLE 7

Under nitrogen, 760 mg (20 mmol) sodium borohydride, 500 mg (0.9 mmol) cobalt (II) phthalocyanine and 1.58 g (10 mmol) p-nitrochlorobenzene are agitated in 50 ml ethanol for 71 hours at 20° C. The reaction mixture is neutralized with 5N hydrochloric acid, and the blue precipitate is centrifuged which is washed out with methanol. The centrifugate collected is concentrated and the residue separated into ether and water. After concentration of the ether phase, dried with potassium hydroxide, 950 mg (74%) p-chloroaniline is obtained.

EXAMPLE 8

Under nitrogen, 1.52 g (40 mmol) sodium borohydride, 250 mg (0.4 mmol) cobalt (II) phthalocyanine and 710 mg (5 mmol) p-chloronitrobenzene are agitated in 25 ml ethanol for 94 hours at 20° C. The brown reaction mixture is neutralized, cooling with ice, with 5N hydrochloric acid, and the blue precipitate is centrifuged which is washed out with methanol. The centrifugate collected is concentrated and the residue separated into ether and water. Concentration of the ether phase, which is dried with potassium hydroxide, produces 610 mg (95%) p-chloroaniline.

EXAMPLE 9

Under nitrogen, 3.2 ml (10 mmol) oleic acid, 400 mg (10 mmol) sodium hydroxide, 1 g (25 mmol) sodium borohydride and 500 mg (0.9 mmol) cobalt (II) phthalocyanine are agitated in 80 ml ethanol for 93 hours at 20° C. The green reaction mixture is neutralized, cooling with ice, with 5N hydrochloric acid, and the blue precipitate is centrifuged which is washed with ethanol. The centrifugate collected is mixed with 50 ml 5N hydrochloric acid extraction is performed with benzene. The benzene phase is washed with water, dried with sodium sulfate and concentrated. The fractional crystallization of the ethanol residue yields 1.2 g (42%) stearic acid as well as 1.3 g (46%) not-yet-converted oleic acid.

EXAMPLE 10

Under nitrogen, 2.66 g (65 mmol) sodium borohydride, 500 mg (0.9 mmol) cobalt (II) phthalocyanine and 810 mg (5 mmol) p-nitrobenzyl cyanide are agitated in 50 ml ethanol for 141 hours at 20° C. The brown reaction mixture is acidified, cooling with ice, with 5N hydrochloric acid, and the blue precipitate is centrifuged which is washed out with water. The centrifugate collected is washed with ether and alkalized with sodium hydroxide. Extraction is accomplished with ether, the extract is dried with potassium hydroxide and concentrated, and 310 mg (46%) B-(p-aminophenyl) ethylamine is obtained.

EXAMPLE 11

Under nitrogen, 1.9 g (50 mmol) sodium borohydride, 250 mg (0.4 mmol) cobalt (II) phthalocyanine and 1.11 g (5 mmol) p-ethyl nitrocinnanate are agitated in 25 ml ethanol for 120 hours at 20° C. The brown reaction mixture is neutralized with 5N hydrochloric acid, cooling with ice, and the blue precipitate is centrifuged which is washed out with methanol. The centrifugate collected is concentrated and the residue separated into ether and water. The ether phase is dried with sodium sulfate and concentrated, thus leaving behind 620 mg (64%) β-(p-aminophenyl) propionic acid ether ester.

EXAMPLE 12

Under nitrogen, 2.85 g (75 mmol) sodium borohydride, 500 mg (0.9 mmol) cobalt (II) phthalocyanine and 1.65 g (10 mmol) p-nitro acetophenone are agitated in 50 ml ethanol for 48 hours at 20° C. The reaction mixture is acidified with 5N hydrochloric acid, cooling with ice, and the blue precipitate is centrifuged which is washed with methanol. The centrifugate collected is concentrated and the residue separated into water and ether. The water phase is alkalized with sodium hydroxide and extraction is accomplished with ether. The ether phase is dried with sodium sulfate and concentrated, leaving behind 1.08 g (79%) α-(p-aminophenyl)-ethanol.

EXAMPLE 13

Under nitrogen, 2.85 g (75 mmol) sodium borohydride, 500 mg (0.9 mmol) cobalt (II) phthalocyanine and 670 mg (10 mmol) crotonic acid nitrile are agitated in 50 ml ethanol for 143 hours at 20° C. The brown reaction mixture is acidified with 5N hydrochloric acid, cooling with ice, and the blue precipitate is centrifuged which is washed out with water and methanol. The centrifugate collected is concentrated and the residue separated into water and ether. The water phase is alkalized with sodium hydroxide, and extraction is performed with ether. The ether phase is extracted with 15 ml 1N hydrochloric acid and 10 ml water, and the acidic extract is concentrated until dry, leaving behind 400 mg (36%) n-butylamine hydrochloride.

EXAMPLE 14

Under nitrogen, 11.4 g (11.6 mmol) dilithium iron (0) phthalocyanine x 5.5 THF and 513 mg (2.32 mmol) p-ethyl nitrocinnamate are agitated in 50 ml ethanol for 1 hour at 20° C. The wine-red reaction mixture is acidified with 5N hydrochloric acid and the blue precipitate is centrifuged which is washed out with ethanol. The centrifugate collected is concentrated and the residue separated into water and ether. The water phase is neutralized with sodium bicarbonate, and extraction is performed with ether. After concentration of the ether extract, dried with sodium sulfate, 280 mg (63%) p-ethyl aminocinnamate is obtained.

EXAMPLE 15

Under nitrogen, 2.85 g (75 mmol) sodium borohydride, 500 mg (0.9 mmol) iron (II) phthalocyanine and 1.02 ml (10 mmol) benzonitrile are agitated in 50 ml ethanol for 162 hours at 20° C. The reaction mixture is acidified with 5N hydrochloric acid, and the blue precipitate is centrifuged which is washed out with ethanol. The centrifugate collected is concentrated and the residue separated into water and ether. The water phase is alkalized with sodium hydroxide, and extraction is performed with ether. Concentration of the ester [SIC] phase, dried with potassium hydroxide, produces 200 mg (19%) benzylamine.

EXAMPLE 16

Under nitrogen, 2.85 g (75 mmol) sodium borohydride, 500 mg (0.9 mmol) manganese (II) phthalocyanine and 1.58 g (10 mmol) p-nitrochlorobenzene are agitated in 50 ml ethanol for 91 hours at 20° C. The reaction mixture is neutralized with 5N hydrochloric acid, and the black precipitate is centrifuged which is washed out with methanol. The centrifugate collected is concentrated and the residue separated into water and ether. Concentration of the ether phase, dried with potassium hydroxide, produces 1.0 g (78%) p-chloroaniline.

EXAMPLE 17

Under nitrogen, 2.85 g (75 mmol) sodium borohydride, 500 mg (0.9 mmol) nickel (II) phthalocyanine and 1.58 g (10 mmol) p-nitrochlorobenzene are agitated in 50 ml ethanol for 70 hours at 20° C. The reaction mixture is neutralized with 5N hydrochloric acid, and the blue precipitate is centrifuged which is washed out with methanol. The centrifugate collected is concentrated and the residue separated into ether and water. Concentration of the ether phase, dried with potassium hydroxide, produces 200 mg (16%) p-chloroaniline.

EXAMPLE 18

Under nitrogen, 2.85 g (75 mmol) sodium borohydride, 500 mg (0.8 mmol) hydroxyvanadium (IV)-phthalocyanine and 1.58 g (10 mmol) p-nitro-chlorobenzene are agitated in 50 ml ethanol for 22 hours at 20° C. The lilac reaction mixture is neutralized with 5N hydrochloric acid, cooling with ice, and the blue precipitate is centrifuged which is washed with methanol. The centrifugate collected is concentrated and the residue separated into water and ether. After concentration of the ether phase, dried with potassium hydroxide, 1.17 g (91%) p-chloroaniline is obtained.

EXAMPLE 19

Under nitrogen, 2.85 g (75 mmol) sodium borohydride, 1.58 g (10 mmol) p-nitrochlorobenzene and 500 mg (1 mmol) bis [2-(1'-imino-3'-isoindolenine)-5-amino-1,3,4thiadiazolato]-cobalt (II) are agitated in 50 ml ethanol for 92 hours at 20° C. The reddish-brown reaction mixture is neutralized with 5N hydrochloric acid, cooling with ice, and is concentrated. The residue is separated into water and ether; the ether phase is dried with potassium hydroxide and concentrated, leaving behind 980 mg (77%) p-chloroaniline.

I claim:

1. Improved method for reduction of reducible groups containing C-atoms or N-atoms or a combination of these, which can be carried out selectively, preserving sensitive, reducible groupings; the improvement being that for optional selective reduction under normal pressure conditions of
   (a) the $NO_2$, NO, or oximen group, there is used a metal macrocyclic in prereduced form, the metal macrocyclic being selected from the group consisting of:
   (1) metallic phthalocyanine, especially of the general formula II

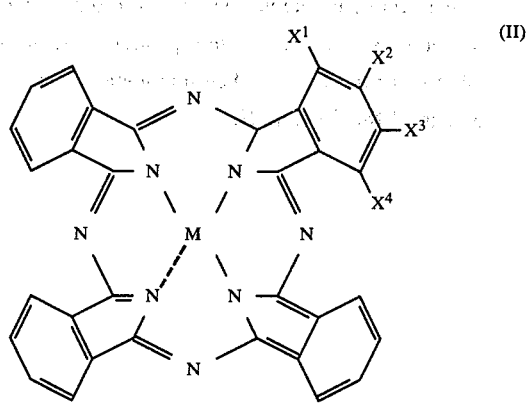

in which $X^{1-4}$ represent H, halogens such as Cl, F, or cyano, (2) a metalporphyrin of the general formula III

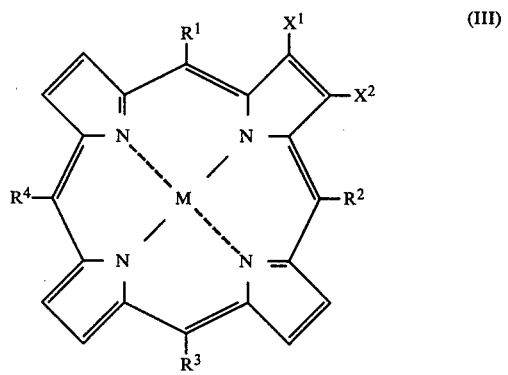

in which $R^1$ to $R^4$ represent H, phenyl or low alkyl and $X^1$, $X^2$ stand for H, halogens such as chlorine, bromine or cyano; and (3) a mixed cycle of the general formula IV

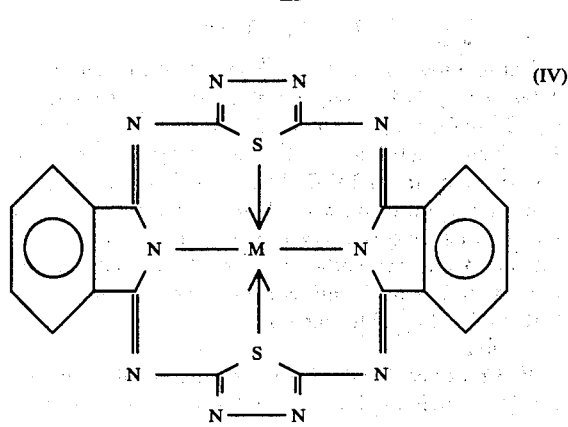

which can be substituted in the benzoid ring with halogens or cyano groups, the metal in the macrocyclic being Fe, Co, Ni, Mn, Ti, V or Cr, which may be in ion form, or (b) the $NO_2$, NO, oxime groups and/or a double-bond, a combination of said metal macrocyclic is used with an additional reducing agent, said additional reducing agent being a sodium boranate, lithium alanate or a reaction product thereof with alcohol or hydrogen, when said metal macrocyclic is one of the formula II.

2. In accordance with claim 1, method characterized by the fact that the metal macrocyclic Co (II)-phthalocyanine exists.

3. In accordance with claim 1, method characterized by the fact that the reaction is carried out in a protective gas.

4. In accordance with claim 1, method characterized by the fact that the reaction is carried out in a protic solvent.

5. In accordance with claim 4, method characterized by the fact that the combination of Co (II)-phthalocyanine and sodium boranate is used as a reducing agent.

6. In accordance with claim 1, method characterized by the fact that in the combination of metal macrocyclic with hydrogen as a reducing agent, work is done in a low temperature range, i.e., between 0° and 30° C.

7. In accordance with claim 1, method characterized by the fact that the reaction is carried out at a neutral or alkaline pH value, preferably in the pH range of 7 to 9.

8. In accordance with claim 1, method characterized by the fact that the reduction of nitriles is carried out in a neutral or alkaline pH range.

9. In accordance with of the claim 1, method characterized by the fact that the reduction of double bonds is carried out with a combination of metal phthalocyanine and a reducing agent selected from among sodium boranate, lithium alanate or their alcoholates, in a solvent or in the presence of hydrogen and at a low temperature.

10. In accordance with claim 1, method characterized by the fact that hydrogenation is accomplished at standard pressure.

* * * * *